United States Patent [19]

Paoletti et al.

[11] Patent Number: 4,477,484
[45] Date of Patent: Oct. 16, 1984

[54] ELECTROLESS PLATING MONITOR

[75] Inventors: Frank Paoletti, Endwell; Steven A. Schubert, Vestal, both of N.Y.

[73] Assignee: International Business Machines Corporation, Armonk, N.Y.

[21] Appl. No.: 448,574

[22] Filed: Dec. 10, 1982

[51] Int. Cl.³ .......................... B05D 1/00; G01R 27/02
[52] U.S. Cl. ..................... 427/10; 324/65 R; 427/96; 427/97; 427/304; 427/305; 427/306; 427/98
[58] Field of Search .......................... 427/10, 304–306, 427/96, 97, 98; 428/901; 174/68.5; 339/17 R, 17 E, 17 T; 324/65 R, 65 CR

[56] References Cited
U.S. PATENT DOCUMENTS 3,134,690  5/1964  Eriksson ........................... 427/306
3,400,014  9/1968  Blumberg et al. .................. 427/10
4,073,964  2/1978  Herrmann ......................... 427/10

Primary Examiner—Norman Morgenstern
Assistant Examiner—Janyce A. Bell
Attorney, Agent, or Firm—Kenneth P. Johnson

[57] ABSTRACT

Apparatus and method for determining the initiation, progression and quality electroless plating of blind or through hole walls in circuit panels. A test coupon for monitoring plating is provided having a sensitized initiation conductivity zone and sensitized through-hole walls arranged in a series resistance circuit with both conductivity zone and series circuit being measured periodically as to resistivity to determine the start or "take" of electroless plating and its progress during continued immersion.

9 Claims, 3 Drawing Figures

ELECTROLESS PLATING MONITOR

BACKGROUND OF THE INVENTION

This invention relates generally to electroless copper plating and more particularly to apparatus for determining the initiation and progression of such plating including plated hole quality.

Autocatalytic or electroless plating of copper is frequently employed to additively construct circuit conductors on printed circuit panels because copper can be deposited directly on non-conducting substrates. Its application, however, requires careful sensitization or seeding of the areas to be plated which comprises a treatment with a solution of a colloidal metal and then an acceleration step to remove inactive components of the colloid from the sensitized dielectric substrate. After suitable rinsing, the circuit panel is immersed in the electroless plating bath which must be maintained within narrow tolerance limits as to components and temperature. The series of baths, the timings, temperatures and the maintenance of bath proportionalities are all critical to the plating process. Although the baths can be analyzed with some degree of accuracy, it is difficult to anticipate the degrees of change upon immersion of substrates and prevent occasional erratic performance.

There are instruments and techniques to determine the approximate status of the bath, but there occur undetected imbalances or variations in both the sensitization process or bath makeup. These variations may cause poor adherence of the seed that results in voids in the plated areas. Plating areas particularly prone to voids are the hole walls of blind or through holes in circuit panels. Because of the length-to-diameter ratio, the circulation of the baths in the holes may not be as thorough thus creating open circuits or voids on the hole walls where no plated metal has adhered.

The panels each may have hundreds or thousands of holes and are immersed in groups in the baths for both the sensitizing and plating steps. There is no known check in maufacturing for judging the quality of the sensitizing step except to attempt the plating. Since the plating is a slow process, the panels cannot be ultimately checked until the prescribed time has elapsed. Thus many panels may conclude full cycles of processing only to be found having voids that render the panels useless, necessitating their discard.

OBJECTS AND SUMMARY OF THE INVENTION

It is accordingly a primary object of this invention to provide a method and apparatus of early detection of the initiation of electroless metal deposition on the part to be plated soon after immersion in the plating bath.

Another object of this invention is to provide a method of determining the progress of electroless plating in blind and through holes in a circuit panel.

A still further object of this invention is to provide a method of monitoring the plating deposited by an electroless plating bath by subjecting a circuitized test coupon to the same plating processing steps concurrently with circuit panels and measuring the electrical conductivity of areas being plated on the coupon as an indicator of the plating quality of the panels.

The foregoing objects are accomplished in accordance with the invention by forming a test coupon of insulative substrate similar to that of circuit panels, drilling the coupon to form a plurality of holes therein, interconnecting the hole walls in series via circuit lines in or on the coupon and providing a pair of auxiliary circuit lines that overlay an area to be plated on the surface of the coupon. The coupon is then subjected to the sensitizing bath and the electroless bath with a group of circuit panels that are to undergo the same processing. The coupon is first connected to instruments for measuring the conductivity of the surface area between the pair of auxiliary circuit lines that will indicate the initiation of plating. Thereafter, the conductivity of the series-connected hole walls is measured periodically. Those conductivity readings can be translated into an indication of plating quality on the hole walls and a deposition rate for plating to thus indicate the hole wall plating has started and is continuing during immersion.

The invention has the advantage of providing an early indication of whether the metal being deposited by the bath is "taking" to the seed via the pair of auxiliary electrodes and sensitized surface area. When such indication occurs at the expected time, measurements of the series circuit can then begin for the hole walls and periodic measurements will provide the rate at which the plating thickness is increasing therein. Voids, of course, can be detected by the indication of abnormally high resistance. This method alerts an operator to the possible malfunction of a plating bath, or inadequately sensitized plating areas without completing the full cycle which may require up to 24 hours and may prevent the loading of subsequent panels in malfunctioning baths.

The foregoing and other objects, features and advantages of the invention will be apparent from the following more particular description of a preferred embodiment of the invention as illustrated in the accompanying drawing.

DESCRIPTION OF THE PREFERRED EMBODIMENT

Figure 1:
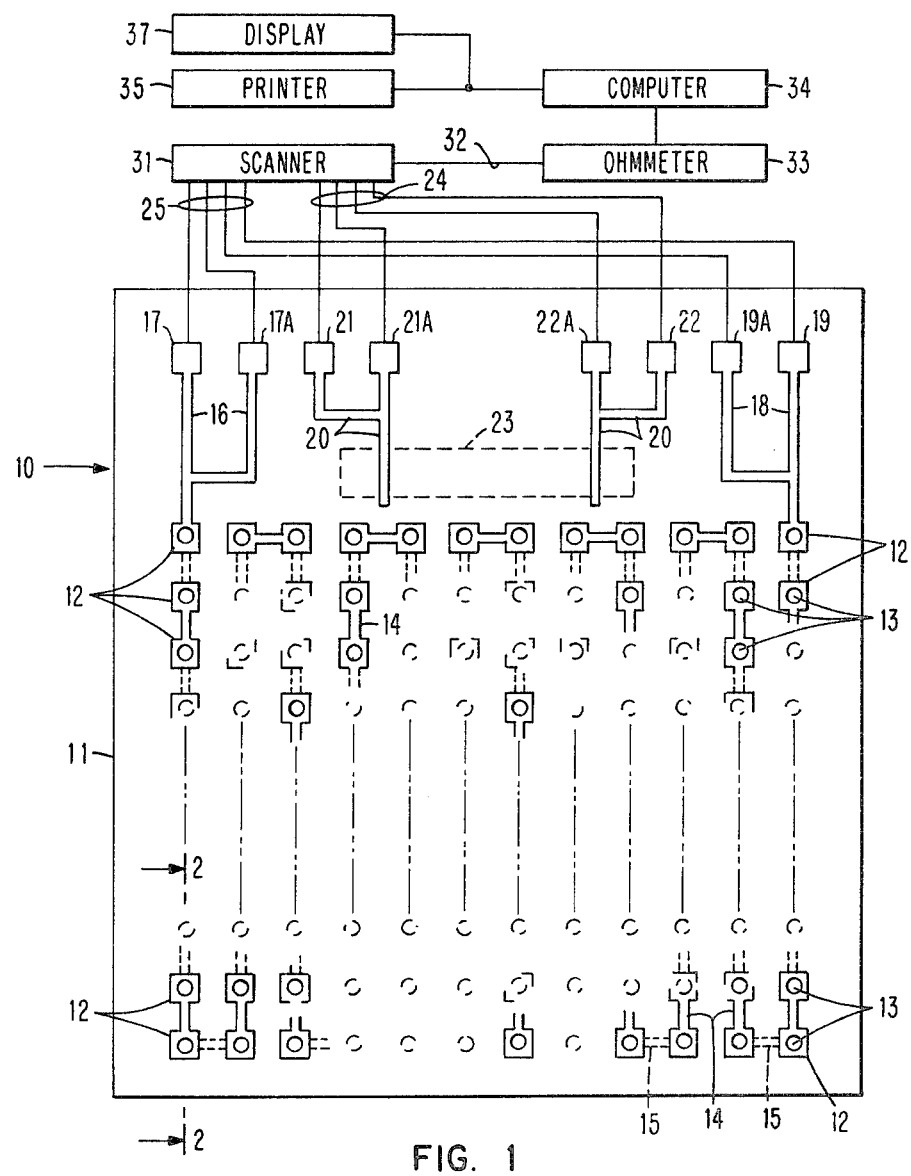
FIG. 1 is a plan view of a test coupon for determining plating quality constructed in accordance with the principles of the invention.
Figure 2:
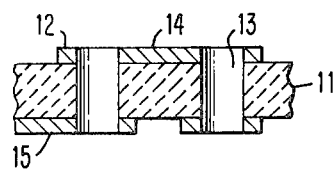
FIG. 2 is a sectional view of through holes taken along the line 2—2 in FIG. 1.

Referring to FIGS. 1 and 2, there is shown a test coupon 10 that is constructed in a manner similar to circuit panels that are to be sensitized and plated. The coupon substrate 11 is preferably formed of glass cloth and epoxy as in the typical circuit panel. Not all layers need to be included in the substrate composite but its thickness should approximate that of the circuit panels with which it is to be processed. Conductive circuit lands 12 are formed in alignment on opposite sides of the coupon at the location of each through-hole 13. The lands are interconnected in an electrical series arrangement by circuit lines 14 on the top and 15 on the bottom of the substrate. Additional circuit lines 16 with lands 17 and 17A and lines 18 with lands 19 and 19A permit the connection of a conductivity measuring instrument to the series circuit. After the lands and lines have been formed, the holes are drilled through each pair of opposing lands to form through-holes having walls which can be sensitized and plated in an electroless plating bath, usually for depositing copper. As the hole walls build up, the opposing lands will be electrically connected by the plating.

The test coupon of the invention is also formed with circuit lines 20, with connection land pairs 21 and 21A and 22 and 22A, which cross a rectangular area 23, indicated in phantom, that will be sensitized for electroless plating at the same time holes 13 are seeded.

After the conductive lines and lands have been formed, the coupon is drilled and subjected to the sequence of sensitizing baths to deposit tin and palladium on the hole walls and surface area 23. Sensitization of the coupon is done in the same manner as the regular panels and preferably at the same time.

In use, a test coupon accompanies each rack of circuit panels to be plated. The coupon is connected by wires to a scanning or multiplexer circuit 31. The scanner can be switched between the wires 24 connecting lands 21 and 22 and wires 25 connecting lands 17 and 19. Resistance readings are preferably made using the four wire Kelvin technique to obtain accurate measurements. These wires are connected through a bus 32 to an ohmmeter 33 which can apply a predetermined constant current between pairs of lands 21 and 22 or between lands 17 and 19. The ohmmeter then reads the voltage drop between lands 21A and 22A or between 17A and 19A to obtain the resistance of the circuit path. The ohmmeter can be further connected to a computer 34, which determines the times for making the resistance measurement with the ohmmeter, and the results of such measurements can be recorded by printer 35 or shown on display 37.

After wires 24 and 25 are connected to the respective lands 17, 19, 21 and 22, the coupon is immersed in the electroless plating bath along with the regular circuit panels to be plated. The coupon is preferably positioned in a representative plating zone. Plating is then allowed to proceed in normal fashion. Conductivity mesurements are first taken for sensitized surface area 23 after immersion of approximately 30 seconds and thereafter at 30 second intervals. As the copper begins to plate to the seeded sites, those sites increase in plated thickness with time and eventually form a relatively low resistance circuit between circuit lines 20 so that a resistance reading can be obtained. This reading indicates that the plating has been initiated and is "taking" and depositing at the sensitized area. Thereafter, the scanner or multiplexer circuit 31 is switched to the circuit comprised of pads 17 and 19 which is the series connected lands and hole walls. During the time that sensitized area 23 was being plated, the hole walls were also being plated at their seeded sites. Resistance measurements of the series circuit of hole walls at regular intervals will provide an indication of the plating quality via the magnitude of the resistance and the rate at which metal is being deposited via the change per unit time. As the metal increases in thickness, the resistance decreases so that the resistance measurements provide a direct indication of the efficiency of the plating process.

The resistance values encountered at identical stages for the series circuits of several coupons will vary. Experience with acceptable coupons, however, will provide a range of values by which the progress of plating can be judged.

Figure 3:
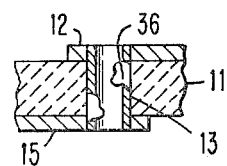
FIG. 3 is a sectional view of a plated through hole wall having plating voids thereon.

Although the hole walls may have plating deposited thereon, a part of the wall of some holes may be devoid of plating, as seen at 36 in FIG. 3. When this occurs, the resistance measurement will be higher then that of an acceptable panel. The use of the test coupon enables an operator to closely estimate the hole quality of the panels during the immersion time. If the resistance is abnormally high, steps can be taken to immediately correct the difficulty before plating subsequent batches of panels, also of poor quality.

The test coupon has been described as formed with through holes. Coupons, however, can be used in which blind holes are formed and the hole walls extend in series between conductors on the coupon surface and other conductors on a buried circuit plane. The monitoring is just as effective and accurate.

Although not necessary in the practice of this invention, the concurrent use of a plating rate monitor is of benefit to enable an estimate of the time that should elapse between immersion and the various stages of plating. By knowing the expected times for reaching certain resistance values, a better idea of the bath plating efficiency can be obtained.

While the invention has been particularly shown and described with reference to a preferred embodiment thereof, it will be understood by those skilled in the art that changes in form and details may be made therein without departing from the spirit and scope of the invention.

What is claimed is:

1. A process for monitoring the progress of electroless plating of sensitized elements comprising the steps of:

forming a coupon of insulative substrate having a plurality of holes with the hole walls interconnected in a series resistance circuit by conductors such that the hole walls are a part of said circuit;

sensitizing the walls of said holes with a solution to initiate the deposit of metal thereon;

immersing said sensitized coupon in an electroless metal plating bath to deposit metal on said walls; and measuring the resistance of said circuit as an indication of the amount of metal plated onto said sensitized hole walls during said immersion.

2. The process as described in claim 1 including the further step of forming a plurality of auxiliary circuit lines on a surface of said coupon intersecting an auxiliary sensitized area on said coupon surface; and determining the time at which said immersed coupon indicates measurable electrical continuity between said auxiliary circuit lines through said auxiliary sensitized area.

3. The process as described in claim 1 wherein said resistance measurements are made at regular intervals to determine a rate of metal deposition on said hole walls.

4. The process as described in claim 2 wherein said series circuit of hole walls is measured for resistance after measurable resistance has been determined for said auxiliary circuit lines.

5. A process for monitoring the progress of electroless plating of elements sensitized to accept said plating comprising the steps of:

forming an insulative panel having a plurality of holes with the hole walls intersecting conductive circuit lands on opposite surfaces of said panel and conductors interconnecting said lands so that said hole walls lie in a series-resistance circuit;

sensitizing said hole walls to initiate plating thereon upon immersion in an electroless metal plating bath;

immersing said sensitized panel in said electroless metal plating bath; and measuring the resistance of said series circuit as an indication of the amount of material plated onto said hole walls during said immersion.

6. A circuitized coupon for monitoring the progress of electroless metal plating in a bath comprising:

a substrate having a plurality of holes having walls sensitized to initiate said electroless metal plating, said walls being connected in series by circuit means between at least a pair of terminals;

a pair of spaced, electrically conductive electrodes on one surface of said panel; and a sensitized area to be plated upon immersion in said bath extending between said electrodes.

7. A circuitized coupon as described in claim 6 further including means for measuring the electrical resistance between said electrodes and through said series of hole walls.

8. A circuitized coupon as described in claim 6 wherein said circuit means includes a plurality of circuit lands on opposite surfaces of said panel each surrounding a said through-hole and circuit lines on said panel surface interconnecting pairs of said lands.

9. The process as described in claim 1 wherein said resistance measurement is made a plurality of times during said electroless plating.

* * * * *